United States Patent
Lee et al.

(10) Patent No.: US 8,894,823 B2
(45) Date of Patent: Nov. 25, 2014

(54) METHOD FOR MANUFACTURING ISOPROPYL ALCOHOL

(71) Applicant: LG Chem, Ltd., Seoul (KR)

(72) Inventors: Sung Kyu Lee, Daejeon (KR); Jong Ku Lee, Daejeon (KR); Joon Ho Shin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/030,646

(22) Filed: Sep. 18, 2013

(65) Prior Publication Data

US 2014/0090971 A1 Apr. 3, 2014

Related U.S. Application Data

(63) Continuation of application No. PCT/KR2013/005739, filed on Jun. 28, 2013.

(30) Foreign Application Priority Data

Jun. 28, 2012 (KR) .................. 10-2012-0070062
Jun. 27, 2013 (KR) .................. 10-2013-0074549

(51) Int. Cl.
| | | |
|---|---|---|
| *B01D 3/14* | (2006.01) | |
| *C07C 29/80* | (2006.01) | |
| *C07C 31/10* | (2006.01) | |
| *B01D 3/32* | (2006.01) | |
| *C07C 31/125* | (2006.01) | |

(52) U.S. Cl.
CPC . *C07C 29/80* (2013.01); *B01D 3/32* (2013.01); *C07C 31/125* (2013.01); *B01D 3/141* (2013.01)
USPC .................. 203/18; 203/87; 203/99; 202/158; 202/161; 202/262; 568/889; 568/913; 568/918

(58) Field of Classification Search
CPC ....... C07C 31/125; C07C 29/80; B01D 3/141
USPC ............... 202/158, 161, 262; 203/18, 87, 99; 568/889, 913, 918
See application file for complete search history.

(56) References Cited

U.S. PATENT DOCUMENTS 7,750,194 B2 * 7/2010 Degen et al. .................. 568/889
7,799,958 B2 * 9/2010 Bonmann et al. ............. 568/881

(Continued)

FOREIGN PATENT DOCUMENTS

| EP | 0728721 | 8/1996 |
| JP | 11-506431 | 6/1999 |

(Continued)

*Primary Examiner* — Nina Bhat
*Assistant Examiner* — Jonathan Miller
(74) *Attorney, Agent, or Firm* — McKenna Long & Aldridge, LLP

(57) ABSTRACT

The present application relates to a method of manufacturing isopropyl alcohol. Isopropyl alcohol with high purity is obtained from a feed including water and isopropyl alcohol. In addition, energy used in a process of obtaining the isopropyl alcohol, and investment cost for manufacturing facilities are reduced.

8 Claims, 1 Drawing Sheet

(56) References Cited

U.S. PATENT DOCUMENTS

| | | |
|---|---|---|
| 2009/0093656 A1* | 4/2009 | Bonmann et al. ............ 568/798 |
| 2010/0099155 A1* | 4/2010 | Frank et al. .................. 435/135 |
| 2011/0303526 A1* | 12/2011 | Lee et al. ....................... 203/81 |
| 2012/0004473 A1* | 1/2012 | Lee et al. ..................... 568/913 |
| 2012/0006673 A1* | 1/2012 | Lee et al. ....................... 203/87 |
| 2013/0284586 A1* | 10/2013 | Lee et al. ....................... 203/99 |
| 2013/0292243 A1* | 11/2013 | Lee et al. ....................... 203/87 |
| 2013/0334029 A1* | 12/2013 | Lee et al. ....................... 203/81 |

FOREIGN PATENT DOCUMENTS

| | | |
|---|---|---|
| KR | 10-1996-0031412 | 9/1996 |
| KR | 10-0561738 | 3/2006 |
| KR | 10-2010-0061790 | 6/2010 |
| WO | 96/36412 | 11/1996 |
| WO | 2013/077700 | 5/2013 |

* cited by examiner

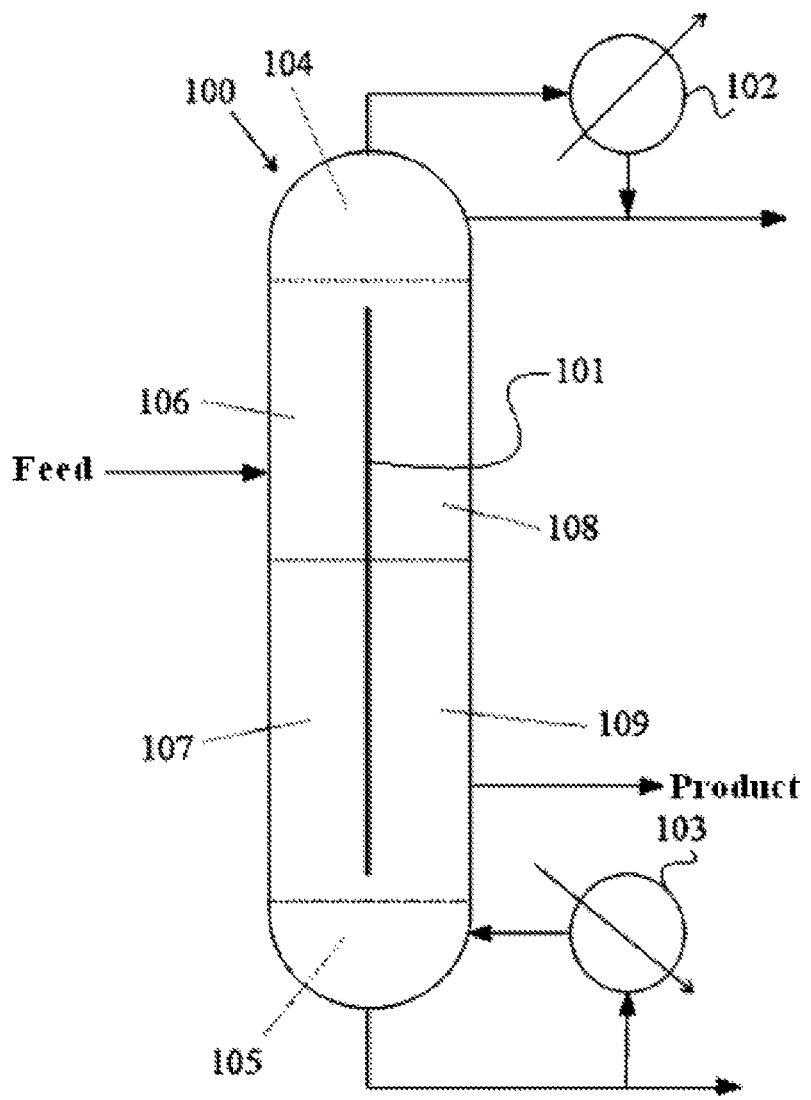

METHOD FOR MANUFACTURING ISOPROPYL ALCOHOL

This application is a Continuation Bypass of International Application No. PCT/KR2013/005739, filed Jun. 28, 2013, and claims priority to and the benefit of Korean Patent Application Nos. 10-2012-0070062, filed Jun. 28, 2012 and 10-2013-0074549, filed Jun. 27, 2013, the disclosures of which are incorporated herein by reference in their entirety.

TECHNICAL FIELD

The present application relates to a method of manufacturing isopropyl alcohol.

BACKGROUND ART

Isopropyl alcohol (IPA) has been used for various purposes, for example, as a cleaner in the electronics industry to fabricate a semiconductor device, a liquid crystal display (LCD), etc.

Isopropyl alcohol, for example, may be fabricated from propylene, acetone, etc. In most cases, since a reactant including isopropyl alcohol is an azeotropic mixture containing water, it is difficult to separate isopropyl alcohol therefrom.

DISCLOSURE

Technical Problem

An objective of the present application is to provide a method of manufacturing isopropyl alcohol.

Technical Solution

This application relates to a method of manufacturing isopropyl alcohol. An exemplary manufacturing method may include supplying a feed including isopropyl alcohol to a dividing wall column (DWC) to be refined in the dividing wall column.

The dividing wall column is an apparatus designed for distilling a feed including three components including a so-called low boiling point material, intermediate boiling point material, and high boiling point material. The dividing wall column is thermodynamically equivalent to a Petlyuk column which is thermally coupled distillation column. The Petlyuk column is designed in such a way that a pre-fractionator and a main column are arranged in a thermally integrated structure, whereby the low boiling point material and the high boiling point material are primarily separated in the pre-fractionator, each of an overhead portion and a bottom portion of the pre-fractionator is introduced to a supply area of the main column, and thereby the low boiling point material, the intermediate boiling point material, and the high boiling point material are separated in the main column. In comparison, the dividing wall column is designed in such a way that the pre-fractionator is integrated inside the main separator by installing a dividing wall in a column.

For example, the dividing wall column may have a structure depicted in FIG. 1. FIG. 1 shows an exemplary dividing wall column 100. As shown in FIG. 1, the exemplary dividing wall column 100 may have a structure of which an interior is divided by a dividing wall 101, and which includes an upper condenser 102, a lower reboiler 103, etc. In addition, the interior of the dividing wall column 100 may be divided into for example, an overhead portion 104, a bottom portion 105, an upper supply area 106, a lower supply area 107, an upper outflow area 108, and a lower outflow area 109, as shown in FIG. 1 which is virtually divided by dotted lines. Here, the term "upper and lower supply areas" may respectively refer to upper and lower areas when an area in which the dividing wall 101 is located, in a space to which the feed is supplied among spaces divided by the dividing wall 101 in the dividing wall column structure, is bisected in a longitudinal direction of the dividing wall column 100. In addition, the term "upper and lower outflow areas" may respectively refer to upper and lower areas when an area in which the dividing wall 101 is located, in a space to which a product is outflowed among the spaces divided by the dividing wall 101 in the dividing wall column structure, is bisected in the longitudinal direction of the dividing wall column 100.

A specific kind of the dividing wall column that is used in a process of distilling isopropyl alcohol is not particularly limited. For example, a dividing wall column with a general structure as shown in FIG. 1, or a dividing wall column of which a location or shape of the dividing wall is designed to be changed in consideration of separation efficiency, may be used. In addition, the number of plate and inner diameter of the dividing wall column are not particularly limited, and may be set, for example, based on a number of theoretical plate that is inferred from a distillation curve considering a feed composition.

In the manufacturing method, the feed introduced into the dividing wall column may include isopropyl alcohol and water. The water content of the feed may be 10,000 ppm or less, 2,500 ppm or less, or 2,200 ppm or less. In addition, the lower limit of the water content in the feed may be 1,000 ppm, for example. In the manufacturing method, since the water content in the feed is a very important factor for energy efficiency of the distillation process, etc., the water content in the feed may need to be adjusted within the above described range. The feed may include isopropyl alcohol and water, and the specific composition is not particularly limited, as long as the water content is controlled within the above-described range. In general, various kinds of impurities may be included in the feed, depending on which method is used to fabricate the feed including isopropyl alcohol, and the impurities may be efficiently removed by the above described method.

The feed, for example, may be supplied to the upper supply area 106 of the dividing wall column. That is, when supplying the feed to the dividing wall column, the efficient refinement of isopropyl alcohol may be possible by supplying the feed to the upper supply area 106, for example, as shown in FIG. 1, in consideration of the feed composition.

The feed introduced by the above described method may be supplied to the dividing wall column at a flow rate of, for example, 5,000 kg/hr to 13,000 kg/hr. In addition, the temperature of the feed supplied to the dividing wall column may be controlled, for example, at 75° C. to 135° C., 80° C. to 100° C., or 85° C. to 95° C. By supplying the feed at the above described flow rate and temperature, appropriate separation efficiency may be achieved.

During the distillation process in which the feed is supplied to the dividing wall column, an operating temperature of an upper part of the DWC may be controlled, for example, at 40° C. to 140° C. or 60° C. to 86° C.

In addition, an operating temperature of a lower part of the dividing wall column may be controlled, for example, to be 170° C. or less, or 121° C. or less. By controlling operating conditions of the dividing wall column as described above, efficient distillation according to the feed composition may be possible. When the operating temperature of the lower part of the dividing wall column is lowered, the operating temperature of the upper part of the dividing wall column may also be lowered and therefore, a cold utility for cooling the upper part may be changed. In this case, there is a problem in that all of already designed process conditions need to be changed. Accordingly, the lower limit of the operating temperature of the lower part of the dividing wall column is not particularly limited in general, as long as the temperature range of the cooling water used for refining isopropyl alcohol is not changed, and may be 25° C. or more, or 30° C. or more, for example.

In the manufacturing method, the operating condition of the dividing wall column, if needed, may be additionally adjusted in consideration of separation efficiency, etc.

For example, in the refining process, the upper operating pressure may be controlled at 0.1 kg/cm$^2$ to 10.0 kg/cm$^2$, or 0.2 kg/cm$^2$ to 1.2 kg/cm$^2$. Under the operation pressure, efficient distillation according to the feed composition may be possible.

In addition, in a normal operation state, the amount of reflux to the dividing wall column of overhead emissions of the dividing wall column may be controlled at 7,000 kg/hr to 22,000 kg/hr, or 8,000 kg/hr to 20,000 kg/hr. In addition, in a normal operation state, the amount of reflux to the dividing wall column of bottom emissions of the dividing wall column may be controlled at 8,000 kg/hr to 26,000 kg/hr, or 9,000 kg/hr to 23,000 kg/hr.

By operating the dividing wall column using the above described method, isopropyl alcohol with high purity may be refined from the introduced predetermined feed. In an embodiment, the product including the isopropyl alcohol may be discharged to the lower outflow area 109 of the dividing wall column after the distillation process. By adjusting an outflow area of the product in such a way, isopropyl alcohol with higher purity may be obtained from the product. In another embodiment, the water content in the product may be 300 ppm or less, 250 ppm or less, 200 ppm or less, or 150 ppm or 100 ppm or less.

Advantageous Effects

According to the present application, isopropyl alcohol with high purity may be obtained from a feed containing water and isopropyl alcohol. In addition, energy used in the process of obtaining isopropyl alcohol, and investment cost of manufacturing facilities may be reduced.

BRIEF DESCRIPTION OF THE DRAWINGS

FIG. 1 is a diagram showing an exemplary dividing wall column.
100: dividing wall column (DWC)
101: dividing wall
102: condenser
103: reboiler
104: overhead portion
105: bottom portion
106: upper supply area
107: lower supply area
108: upper outflow area
109: lower outflow area

BEST MODE FOR CARRYING OUT THE INVENTION

Hereinafter, the present application will be described in more detail, referring to Example of the present application and Comparative Examples. However, it should be noted that the scope of the present application is not restricted to these Examples.

Example 1

A refining process was performed by supplying a feed including isopropyl alcohol to a dividing wall column having a structure shown in FIG. 1. A number of theoretical plate calculated from a distillation curve considering a feed composition was used as a number of plate of the dividing wall column. A feed including 97.5 wt % to 98.5 wt % of isopropyl alcohol, 0.5 wt % to 1.0 wt % (5,000 ppm to 10,000 ppm) of water content, and 0.3 wt % to 1.0 wt % of other impurities containing ethyl alcohol, etc. was used. As shown in FIG. 1, the refining process was performed by introducing the feed into an upper supply area of the dividing wall column. When introducing the feed into the upper supply area of the dividing wall column, the flow rate was maintained at about 6,250 kg/hr, and the temperature of the feed was maintained at about 90° C. In a steady state, the refinement was carried out while maintaining the operating pressure of an upper part of the dividing wall column at about 1.1 kg/cm$^2$, the operating temperature of the upper part at about 73° C., and the operating temperature of the lower part at about 108° C. Products including refined isopropyl alcohol were obtained at a lower outflow area of the dividing wall column.

Example 2

The refining process was carried out in the same mode as in Example 1 except that a feed having 0.25 wt % (2,500 ppm) of the water content was used.

Example 3

The refining process was carried out in the same mode as in Example 1 except that the operating temperature of the upper part of the dividing wall column was 40° C.

Example 4

The refining process was carried out in the same mode as in Example 1 except that the operating temperature of the upper part of the dividing wall column was 140° C.

Comparative Example 1

The refining process was carried out in the same mode as in Example 1 except that the operating temperature of the upper part of the dividing wall column was 35° C.

Comparative Example 2

The refining process was carried out in the same mode as in Example 1 except that the operating temperature of the upper part was of the dividing wall column was 150° C.

Comparative Example 3

The refining process was carried out in the same mode as in Example 1 except that the operating temperature of the lower part of the dividing wall column was 85° C. In this case, although calorie consumption itself was small, the temperature of the cooling water used in a condenser was significantly lowered, and therefore, there was a problem in that a process design condition had to be changed.

Comparative Example 4

The refining process was carried out in the same mode as in Example 1 except that the operating temperature of the lower part of the dividing wall column was 180° C.

Comparative Example 5

The refining process was carried out in the same mode as in Example 1 except that a feed having 1.1 wt % (11,000 ppm) of the water content was used.

Compositions of products obtained by performing the refining processes of the Examples and Comparative Examples, and calorie consumptions of the reboiler and condenser in each process are shown in Table 1.

TABLE 1

|  |  | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|---|
| Product Composition | IPA | 99.978 wt % | 99.978 wt % | 99.978 wt % | 99.978 wt % | 99.978 wt % | 99.975 wt % | 99.978 wt % | 99.978 wt % | 99.980 wt % |
|  | Water | 100 ppm | 100 ppm | 100 ppm | 100 ppm | 100 ppm | 100 ppm | 100 ppm | 100 ppm | 100 ppm |
|  | Others | 120 ppm | 120 ppm | 120 ppm | 120 ppm | 120 ppm | 150 ppm | 120 ppm | 100 ppm | 100 ppm |
| Reboiler Heat duty |  | 2.28 Gcal/hr | 2.24 Gcal/hr | 2.30 Gcal/hr | 2.31 Gcal/hr | 2.36 Gcal/hr | 2.47 Gcal/hr | 2.31 Gcal/hr | 2.50 Gcal/hr | 11.16 Gcal/hr |
| Condenser Heat duty |  | 2.01 Gcal/hr | 1.97 Gcal/hr | 2.18 Gcal/hr | 2.18 Gcal/hr | 2.23 Gcal/hr | 2.34 Gcal/hr | 2.13 Gcal/hr | 2.37 Gcal/hr | 10.92 Gcal/hr |

The invention claimed is:

1. A method of manufacturing isopropyl alcohol, comprising:

introducing a feed comprising isopropyl alcohol and water into an upper supply area of a dividing wall column, wherein the water content of the feed is 1,000 to 10,000 ppm;

distilling the feed while maintaining an operating temperature of an upper part of the dividing wall column at 40° C. to 140° C. and an operating temperature of a lower part of the dividing wall column at 170° C. or less; and obtaining a product comprising isopropyl alcohol from a lower outflow area of the dividing wall column.

2. The method of claim 1, wherein the water content in the feed is 2,500 ppm or less.

3. The method of claim 1, wherein the flow rate of introduction of the feed is controlled at 5,000 kg/hr to 13,000 kg/hr.

4. The method of claim 1, wherein the temperature of the feed is controlled at 75° C. to 135° C.

5. The method of claim 1, wherein the operating temperature of the upper part of the dividing wall column is controlled at 60° C. to 86° C.

6. The method of claim 1, wherein the operating temperature of the lower part of the dividing wall column is controlled at 121° C. or less.

7. The method of claim 1, wherein an operation pressure of the upper part of the dividing wall column is controlled at 0.1 kg/cm$^2$ to 10.0 kg/cm$^2$.

8. The method of claim 1, wherein the water content of the product is 300 ppm or less.

* * * * *